United States Patent
Hamilton

(10) Patent No.: US 9,739,712 B2
(45) Date of Patent: Aug. 22, 2017

(54) CONTROLLED RAIN AND FOG TESTING APPARATUS

(71) Applicant: The United States of America as represented by the Secretary of the Navy, Washington, DC (US)

(72) Inventor: John S. Hamilton, Solsberry, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/395,424

(22) Filed: Dec. 30, 2016

(65) Prior Publication Data

US 2017/0108434 A1 Apr. 20, 2017

Related U.S. Application Data

(63) Continuation-in-part of application No. 14/225,540, filed on Mar. 26, 2014.

(51) Int. Cl.
| | |
|---|---|
| *G01N 21/53* | (2006.01) |
| *G01M 11/00* | (2006.01) |
| *G01W 1/00* | (2006.01) |
| *F41H 9/06* | (2006.01) |
| *A63J 5/02* | (2006.01) |

(Continued)

(52) U.S. Cl.
CPC .......... *G01N 21/534* (2013.01); *A01G 15/00* (2013.01); *A63J 5/025* (2013.01); *F41H 9/06* (2013.01); *G01M 11/00* (2013.01); *G01N 21/538* (2013.01); *G01W 1/00* (2013.01); *G01J 2001/4247* (2013.01)

(58) Field of Classification Search
CPC .......... A63J 5/025; F41H 9/06; G01N 21/534; G01N 21/538; G01N 21/59; G01W 1/00; G01W 1/02; G01M 11/00; G01J 1/10; G01J 1/18; G01J 1/38; G01J 1/40; G01J 1/4257; G01J 2001/444; A01G 15/00

See application file for complete search history.

(56) References Cited

U.S. PATENT DOCUMENTS

| | | | | |
|---|---|---|---|---|
| 2,695,976 A | * | 11/1954 | Hasenkamp | ......... A01G 25/167 200/61.05 |
| 3,035,777 A | * | 5/1962 | Bodell | ................... A01G 25/00 239/201 |

(Continued)

*Primary Examiner* — Gordon J Stock, Jr.
(74) *Attorney, Agent, or Firm* — Christopher A. Monsey

(57) ABSTRACT

A rain and fog testing apparatus, comprising a fluid channel that runs between a first fluid shutoff coupler and a second fluid shutoff coupler and has at least one dispersion head fluidly coupled to the fluid channel. A liquid pump can be fluidly coupled to the fluid channel at an output end. A liquid heater may also be fluidly coupled to the system along with a controller that provides electrical control of the first fluid shutoff coupler, the second fluid shutoff coupler, the dispersion head, the liquid pump, and the heater. Further, the second fluid shutoff coupler is capable of fluidly coupling a first fluid channel to a plurality of fluid channels and the controller can adjust the orientation of the first fluid shutoff coupler, the second fluid shutoff coupler, the dispersion head, the liquid pump, and the liquid heater to create a simulation of a plurality of rain or fog events.

7 Claims, 5 Drawing Sheets

US 9,739,712 B2

Page 2

(51) Int. Cl.
*A01G 15/00* (2006.01)
*G01J 1/42* (2006.01)

(56) References Cited

U.S. PATENT DOCUMENTS

| | | | | |
|---|---|---|---|---|
| 3,140,720 A | * | 7/1964 | Griswold | A01G 25/162 137/59 |
| RE27,041 E | * | 1/1971 | Hotchkin | A01G 25/162 137/624.2 |
| 3,599,867 A | * | 8/1971 | Griswold | A01G 25/162 137/78.3 |
| 4,185,650 A | * | 1/1980 | Neves | A01G 25/16 137/15.01 |
| 4,244,022 A | * | 1/1981 | Kendall | G04G 15/006 137/624.2 |
| 4,508,269 A | * | 4/1985 | Davis | A01G 25/092 239/729 |
| 4,545,396 A | * | 10/1985 | Miller | A01G 25/16 137/78.3 |
| 5,154,349 A | * | 10/1992 | Vaughn | A01G 25/16 137/624.2 |
| 5,249,745 A | * | 10/1993 | Bertolotti | A01G 25/165 137/624.14 |
| 5,748,466 A | * | 5/1998 | McGivern | G05B 19/0423 239/63 |
| 5,927,603 A | | 7/1999 | McNabb | |
| 6,286,765 B1 | * | 9/2001 | Byles | A01G 25/165 137/624.2 |
| 6,314,340 B1 | * | 11/2001 | Mecham | A01G 25/167 239/69 |
| 6,626,052 B1 | | 9/2003 | Martin et al. | |
| 6,685,104 B1 | | 2/2004 | Float et al. | |
| 7,095,957 B1 | | 8/2006 | Britz et al. | |
| 7,383,721 B2 | * | 6/2008 | Parsons | A01G 25/16 73/46 |
| 7,403,840 B2 | * | 7/2008 | Moore | A01G 25/16 700/282 |
| 8,495,965 B1 | | 7/2013 | Hadida et al. | |
| 9,226,443 B2 | | 1/2016 | Duncan et al. | |
| 2002/0002425 A1 | * | 1/2002 | Dossey | G01F 1/44 700/284 |
| 2006/0278728 A1 | | 12/2006 | Kates | |
| 2011/0088315 A1 | * | 4/2011 | Donoghue | A01G 25/16 47/48.5 |
| 2012/0168528 A1 | | 7/2012 | Hillger et al. | |
| 2012/0175425 A1 | | 7/2012 | Evers et al. | |
| 2012/0279731 A1 | | 11/2012 | Howard, Sr. | |
| 2013/0119150 A1 | | 5/2013 | Cesak et al. | |
| 2013/0126635 A1 | * | 5/2013 | Klinefelter | B05B 12/006 239/76 |
| 2013/0162813 A1 | | 6/2013 | Stephanson | |
| 2014/0236552 A1 | | 8/2014 | Felemban | |
| 2014/0346099 A1 | * | 11/2014 | Brantley | A01G 25/00 210/127 |

* cited by examiner

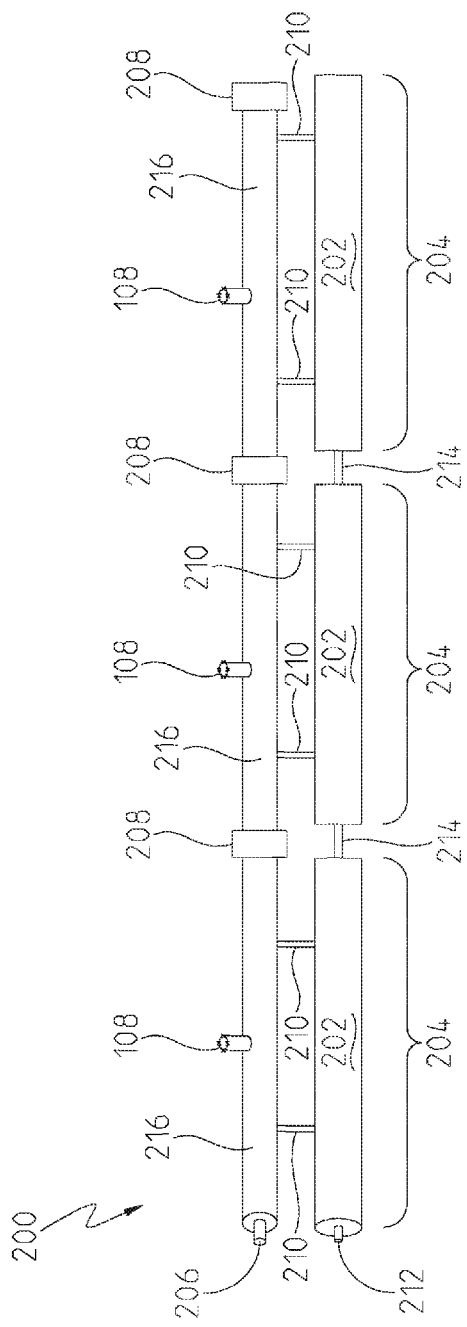
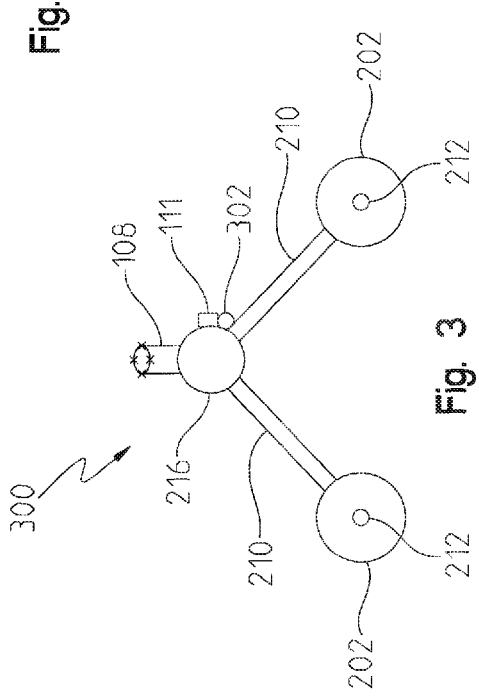
Fig. 2
Fig. 3

CONTROLLED RAIN AND FOG TESTING APPARATUS

CROSS-REFERENCE TO RELATED APPLICATIONS

This application is a continuation-in-part of and claims priority to U.S. patent application Ser. No. 14/225,540, filed Mar. 26, 2014, entitled "CONTROLLED RAIN AND FOG TESTING APPARATUS", the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,401) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND

The present invention relates to a system and apparatus for testing of lasers, lasers accessories and electro-optical devices such as cameras, thermal imagers, and other vision devices. One of issue associated with testing these devices is how well the devices work in the rain or fog. One valuable aspect of testing these devices is determining consistently how far the devices may penetrate through various external conditions. For instance, how well an image can be seen through rain or fog and how much information a laser can transmit through the rain or fog. Another important aspect for testing these devices is ensuring an accurate correlation between an actual and simulated type of rain or fog that electro-optical devices are being tested in. For example, was it a light drizzle, a torrential downpour, or a condition in the middle?

SUMMARY

An exemplary rain and fog testing system may operate on a body of water and may not add to water that is being moved through the rain and fog machine. Such an embodiment can be ideal because it does not create any runoff or pollution problems. One exemplary design can be scalable so that a small to large body of water can be used. One exemplary design may consist of a pipe with a nozzle every 10-feet. In this example, each nozzle can be an individually controlled electro-mechanical screw type solenoid. Such a control system may allow each nozzle to be individually turned on or off. A nozzle hat may create a spray pattern that is controlled via the solenoid. An exemplary combination, such as using the nozzle hat/solenoid combination, may allow a spray pattern to be adjusted from primarily in a vertical to one that sprays primarily in a horizontal orientation. Embodiments of the invention can allow gravity to pull sprayed water downward and more closely mimic effects of rain. The exemplary system with adjustable nozzle combinations may also allow for real time adjustments that may incorporate wind effects on the spray pattern. Exemplary nozzles may be spaced and designed to have overlap to eliminate, as much as possible, dry spots and to promote uniformity in the rain pattern. Exemplary system pipe may be connected to a manifold that allows various size pumps to be used to pump water to exemplary system and its nozzles. Small pumps for fog, large pumps for torrential downpours, and intermediate pumps for precipitation in between the two extremes. Alongside the main pipe that carries water may be a secondary pipe that supplies power and control to the various nozzles. An exemplary secondary pipe may also contain power and controls to activate shutoff valves that can be used to shorten or lengthen the main water pipe.

An ability to create realistic fog may be accomplished by one embodiment which includes a hot water heater. The exemplary hot water heater may heat water to a temperature greater than a surrounding air and water temperature. Hot water may then be sprayed through the nozzles as a fine mist. The hot water and cold air may create fog. Another exemplary system can include an air temperature control system which could include cooling coils or other systems which control air surrounding the nozzle spray areas.

Exemplary design can include at least two basic designs for a rain/fog machine. A first example may require a user to place all of system pipes on either pillars or suspended from a suspension system. In this exemplary case, all of the nozzles may point downward and/or at an angle away from the support structure to provide a consistent rain pattern free of any rain shadows caused by the structure itself.

A second possible design may include a submersible/floatable system that may be capable of creating an unobstructed surface on a body of water. In the case of the submersible/floatable system example, there may be two extra pipes alongside the main pipe. The two extra pipes may be filled with air to float and with water to allow the system to submerge. The rain nozzles may point upward and away from the pipe assembly to provide an unobstructed rain pattern.

Advantages of one exemplary system include an ability for testing electro-optical, infrared, and similar systems on a realistic scale in a realistic environment. System generated rain or fog can be repeated with similar characteristics improving accuracy or rigor arising from repeated testing of new designs.

Variants of the invention can include a mechanism operable for fine-tuned control of artificially generated precipitation that may include a light fog to heavy fog and from a light drizzle to a torrential downpour. By allowing all of the dispersed fluid to fall back into a body of water from where it came from, and by not adding chemicals or substances to the body of water as it is pumped through the system, pollution will be reduced or eliminated.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 2 is one embodiment of the present disclosure that shows multiple sections each utilizing buoyancy devices for support;

FIG. 3 is a front side view of the embodiment of FIG. 2;

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
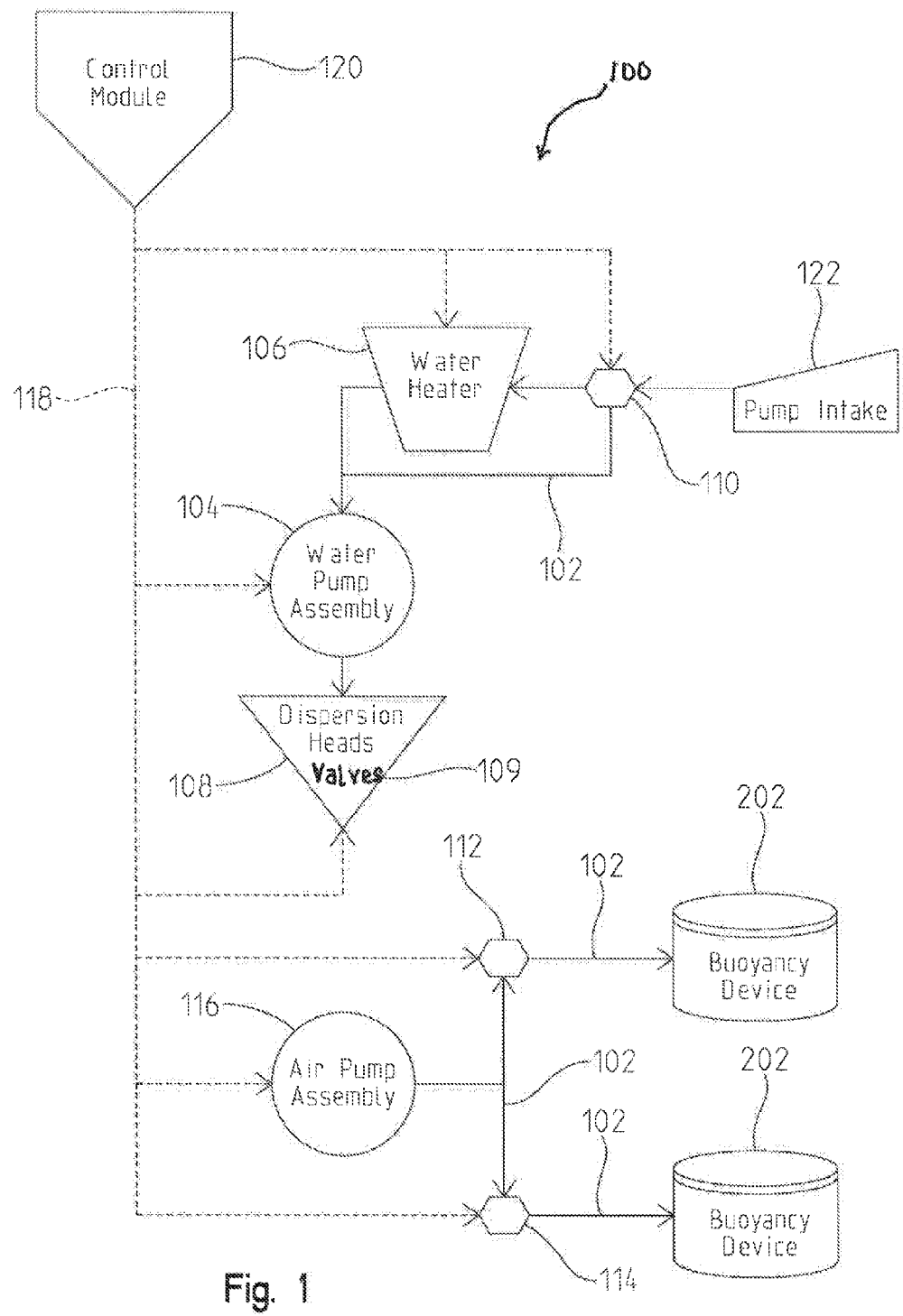
FIG. 1 is a flow chart of one embodiment of the current invention indicating electronic coupling with a dotted line and fluid coupling with a solid line.

FIG. 1 illustrates a flow chart of one embodiment of a rain and fog testing machine 100. More specifically, FIG. 1 shows a series of fluid couplers 102, a first pump 104, a heater 106, electro-mechanically controlled dispersion heads 108, a first valve 110, a second valve 112, a third valve 114, a second pump 116, and electronic couplers 118 coupling the electronic components to a controller 120. The exemplary controller 120 may be electronically coupled to the heater 106, the first valve 110, the first pump 104, the dispersion heads 108, the second valve 112, the second pump 116, and the third valve 114 via the electronic couplers 118. The controller 120 can electronically control an orientation of the first, second, or third valves 110, 112, 114, power to the heater 106, power to the first and second pump 104, 116, and disposition of the dispersion heads 108 to provide a simulation of a rain or fog event that is desired by the user which closely approximates an actual fog or rain condition.

The first pump 104 may be fluidly coupled to a pump intake 122 through the first valve 110. The first valve 110 may further have a first position and a second position that can direct the fluid from the pump intake 122 directly to the first pump 104, or through the heater 106 where the fluid may be heated before entering the first pump 104. Further, the controller 120 may control the first valve 110 to ensure the appropriate fluid coupling of the system per a user's input. For example, if the user desired a fog event, the controller 120 may send an electronic signal to the first valve 110 to ensure the first valve 110 directs the intake fluid through the heater 106 before engaging the first pump 104 to pump fluid to the dispersion heads 108. Further, if the user indicated a desire for a rain event, the controller may send a signal to the first valve 110 directing the first valve 110 to become oriented in a position that may bypass the heater 106 and fluidly couple the pump intake 122 directly to the first pump 104.

The controller 120 may also control the dispersion heads 108 to create the user-desired event. In one embodiment, the dispersion heads 108 may be an electromechanical screw-type solenoid or valve 109 that is capable of dispersing fluid at varying rates. The controller 120 may control the dispersion heads 108 by adjusting the screw-type solenoids or valves 109 to positions that correspond to user inputs. For instance, when the user desires a light rain or fog, the dispersion heads 108 may be adjusted by the controller 120 to a very low flow-rate position. Similarly, if the user desires a heavy rain, the controller 120 may instruct the dispersion heads 108 to become disposed in a high flow rate position.

In addition to adjusting the dispersion heads 108 to control desired environmental event conditions, the controller 120 may also vary the first pump 104 output. For example, if a light rain event is desired by the user, the controller 120 may communicate to the first pump 104 to operate at a lower flow-rate. The lower flow-rate of the first pump 104 could result in the desired light rain event. Correspondingly if the user desires a heavy rain event, the controller 120 may send a signal to the first pump 104 to run at a maximum flow-rate. While both the first pump 104 and the dispersion heads 108 can be adjusted independently from one another to adjust the desired event conditions, one skilled in the art would also understand how both the dispersion heads 108 and the first pump 104 could be simultaneously adjusted to provide the user more resolution in creating specific events. Further, there may be a plurality of dispersion heads located in along the rain and fog testing machine 100 that may each be controlled independently from one another by the controller 120 to create various rain events along the rain and fog testing machine 100.

FIG. 2 shows one embodiment containing multiple sections 200 that utilizes one or more buoyancy devices 202 to elevate the dispersion heads 108 above an underlying body of water 200. In one embodiment, there may be one or more sections 204 that can be coupled to one another to create a rain event for a desired length. For example, each section 204 could be capable of functioning when coupled to the first and second pump 104, 116 whether there is only one section 204 or a plurality of sections 204 coupled to one another. One embodiment can have sections 204 that contain the buoyancy device 202, the dispersion head 108, a fluid coupler 206, a fluid shutoff coupler 208, buoyancy supports 210, an air coupler 212, and an air shutoff coupler 214.

In an embodiment when only one section 204 is utilized, the first pump 104 may be coupled to the fluid coupler 206 to supply fluid to the section 204. Further, the second pump 116 may be coupled to the air coupler 212 to supply air or any other gas/buoyant substance to the buoyancy device 202. The fluid shutoff coupler 208 could be oriented in a closed position when it is not coupled to a further section 204 where the fluid shutoff coupler 208 would not allow fluid to exit a fluid passage 216 through the shutoff coupler 208 end. When fluid is supplied to the fluid passage 216 from the first pump 104, it could be forced out the one or more dispersion heads 108 fluidly coupled to the fluid passage 216 of the section 204.

The fluid passage 216 may be mechanically coupled to the buoyancy devices 202 to allow the fluid passage 216 to be raised above, or lowered into a body of water. One embodiment achieves such functionality by coupling the air coupler 212 to the second pump 116. Further the controller 120 can control both the second pump 116 and the air shutoff coupler 214 to fill the buoyancy device 202 with air or some other buoyant substance or to allow the buoyancy device 202 to fill with water. For example, the user may desire to submerge the section 204 so that the surface of the body of water may be substantially unobstructed by the rain and fog testing machine 100. The section 204 may be submerged when the controller 120 opens the air shutoff coupler 214 to allow water into the buoyancy device 202 while simultaneously opening the air coupler to allow any existing air in the buoyancy device 202 to exit through the air coupler 212. Once a significant enough amount of water has entered the buoyancy device 202, it may sink to the water source bed, leaving the surface unobstructed.

Similarly, when operation of an exemplary rain and fog testing machine 100 is desired by a user, user input provided to the controller 120 can initiate a raising sequence for the buoyancy device 202. The exemplary raising sequence can include opening air coupler 212 and air shutoff coupler 214 and engaging the second pump 116. The second pump 116 may then force air into the buoyance device 202 through the air coupler 212 as water is forced out through the shutoff coupler 214. Once enough water is forced out of the buoyance device 202, the dispersion heads 108 may be elevated above the surface of the surrounding water and the controller may shut the air coupler 212, the shutoff coupler 214, and disengage the second pump 116 to allow the buoyancy device to maintain buoyancy.

While the functionality of one embodiment utilizing one section 204 has been described, FIG. 2 shows how multiple sections 204 can be coupled to one another to achieve substantially the same or desired function(s) on a larger scale. A first section 204 can be coupled to the first pump 104 and the second pump 116 on one end, and to a second section 204 at the other. The shutoff coupler 208 of the first section may become disposed in an open position when it is coupled to a second section 204 to allow fluid to pass through the first fluid passage 216 and into the second fluid passage 216. The fluid coupler 206 of the second section may become fluidly coupled to the shutoff coupler 208 of the first section. Similarly the air shutoff coupler 214 of the first section 202 may fluidly couple to the air coupler 212 of the second buoyancy device 202. Each section 204 may further be hingedly coupled to the previous section 204 to allow for the sections 204 to become angularly offset to one another in the event of rough waters or uneven underlying terrain.

FIG. 3 illustrates a front side view 300 of one embodiment of the present invention. An embodiment could utilize two buoyancy devices 202 to stabilize the fluid passage 216. The buoyancy members 202 could be rigidly coupled to the fluid passage 216 by the buoyancy supports 210 and be offset from the fluid passage 216 on either side to prevent the fluid chamber 216 from overturning in the water.

FIG. 3 also shows an electronic coupler channel 302 located along the exterior of the fluid chamber 216. The electronic coupler channel 302 can provide a watertight routing location for all of the electronically coupled components. Further, watertight connectors (not shown) can be located at each section 204 to allow each section to be electronically coupled to one another. One skilled in the art could understand that there are many ways to protect electronic components from water damage and the electronic coupler channel 302 should not be limited to any one water protective structure. An exemplary design including a water tight chamber allowing an exemplary electronic coupler to pass through, utilizing electronic couplers designed for use in water and the like can also be included.

The embodiments shown and explained in FIG. 2 and FIG. 3 can be ideal because they allow for a rain event to be created for a plurality of different lengths depending on the number of sections 204 coupled to one another and the size of the body of water that they are located on. In one embodiment, a 300 foot combination of sections could be disposed on a body of water for rain and fog testing. The sections 204 could be fluidly and electronically coupled to one another and utilize one first pump 104, one second pump 116, and one water heater 104 for the entire assembly. The first pump 104 could be stored in a pump house and have a pump intake 122 that draws water from the body of water the sections 204 are located on. The controller 120 could also be located in the pump house and allow a user to initiate the desired rain or fog event from the pump house. Further, one skilled in the art could understand that a plurality of pumps and heaters may be necessary for larger applications and this embodiment should not be limited to just one. Another embodiment could have a mile long rain and fog test machine that utilizes pumps every thousand feet to ensure adequate water pressure/temperature for the assembly. The controller could then be adapted to control each pump along the assembly similarly as described herein.

In the 300-foot embodiment, once the user initiates the desired event, the controller 120 can initiate the first pump 104 which can then pump fluid through each of the sections 204 in the assembly to create the desired event along the entire 300 foot combination of sections 204. Further, the controller can open the air shutoff coupler 214 on the last buoyancy device 202, the air coupler 212 of the first buoyancy device 202 and engage the second pump 116 to pump air through all of the fluidly coupled buoyancy devices 202. The pumped air may force any water remaining in the buoyancy devices 202 to be ejected out of the final air shutoff coupler 214. Further, the controller 120 may also communicate with a tip sensor 111 and adjust the air in the buoyancy devices 202 to allow the dispersion heads 108 to be oriented in a desired angular orientation relative to the underlying water by pumping less air into one side of buoyancy devices than the other.

Figure 4:
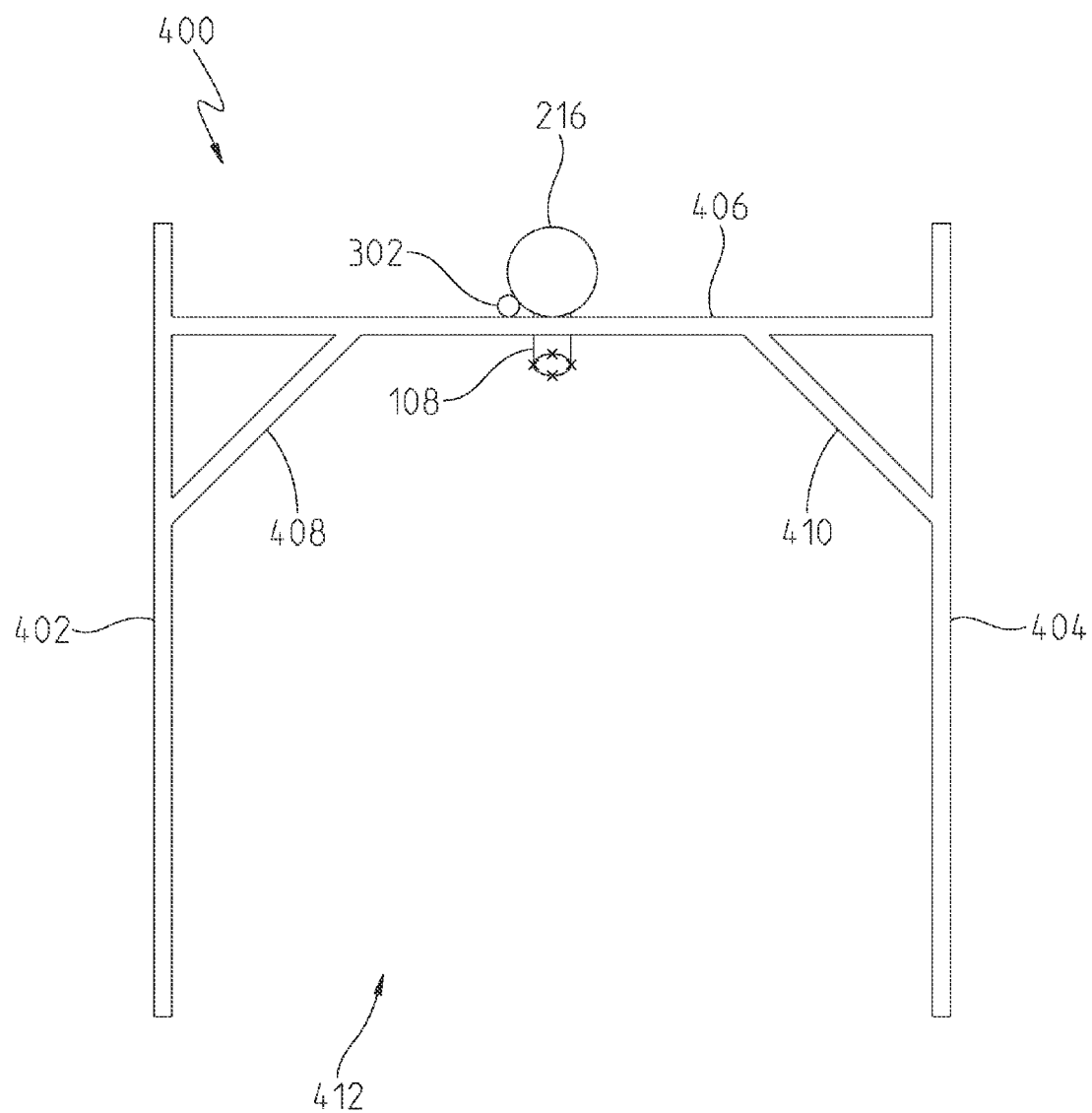
FIG. 4 is another embodiment of the present disclosure that utilizes a fixed support system.

FIG. 4 illustrates one embodiment that may utilize a fixed support structure 400. More particularly, a first member 402 and a second member 404 can be parallel to one another and coupled to one another by a cross member 406. A first and second cross member support 408 and 410 may also couple the first and second member 402, 404 to the cross member 406. In this embodiment, the first and second member 402, 404 may rest on an underlying surface to support the fluid passage 216 and the electronic coupler channel on the cross member 406. The underlying surface could be the bed of a lake, pond, or river, or it could be a pool or manmade structure designed for an exemplary embodiment. In this example, the dispersion heads 108 could dispense liquid downward from the cross member 406 and create an interior region 412 where the testing event will be simulated. Such a design can utilize substantially all of the coupling features described herein to couple multiple sections 204 to one another. A number of fixed support structures 400 could be aligned with one another to create a rain or fog test for a number of system structure lengths.

A variety of mounting variants can be used with exemplary embodiments of the. For instance, a single support could be coupled to the ground with the fluid passage 216 coupled to the distal end. Dispersion heads 108 could be angled to create a desired simulated rain event off to one side of the single support to avoid an undesired consequence of a support inhibiting electro-optical testing or device under test results. A variety of structures could be used to support fluid passages.

Figure 5:
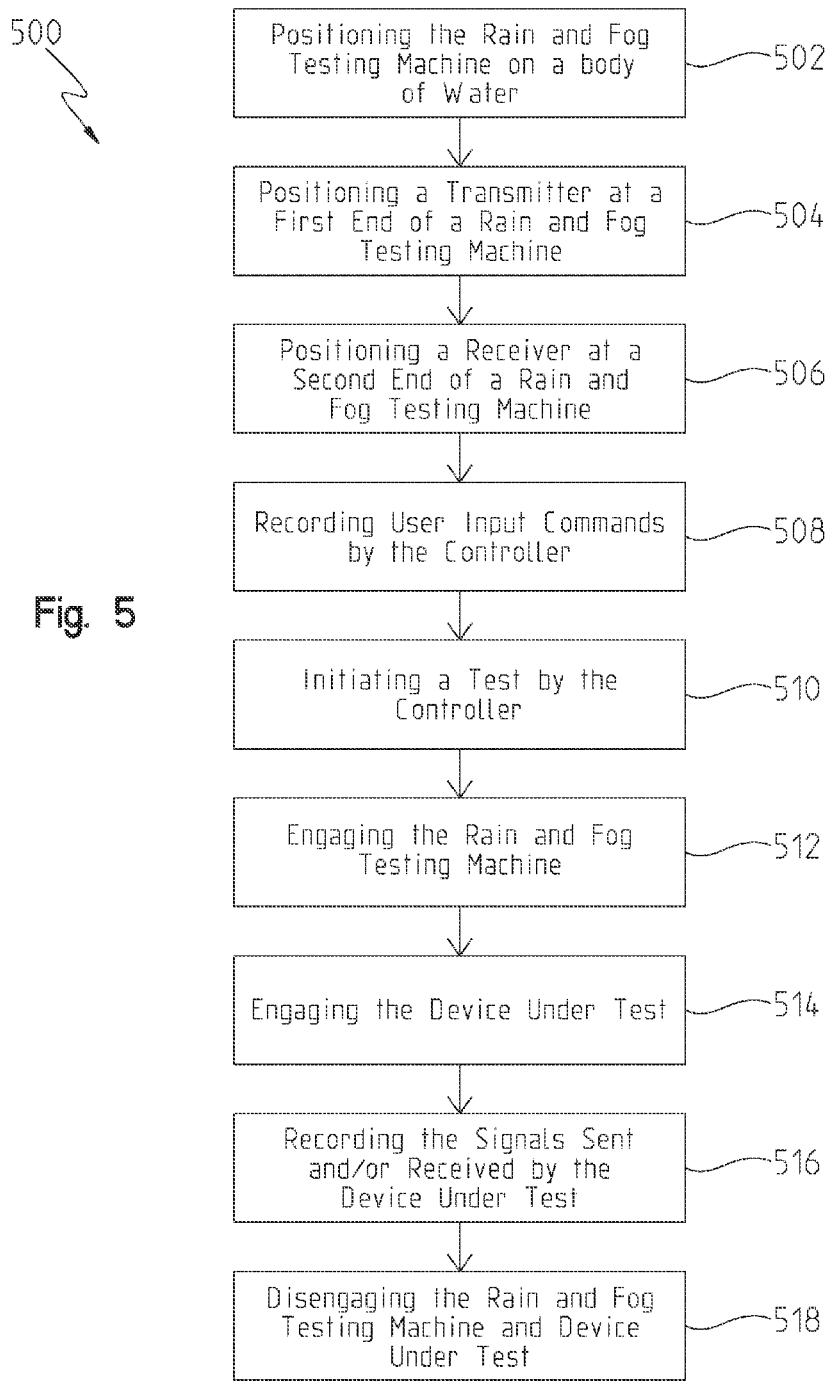
FIG. 5 shows an exemplary method of use of one embodiment of the invention with respect to a body of water.

FIG. 5 illustrates one process that could be utilized to execute a test for a device 500. A first step 502 involves positioning the rain and fog machine 100 on an adequate body of water for linear alignment that will accommodate the type of test that is going to be run. For instance, if the test requires testing a rain event over five-hundred feet, the body of water and the number of sections 204 must be sufficient to accommodate such a test. A second step 504 involves positioning a transmitter, e.g., an electro-optical system or laser, at a first end of the rain and fog machine 100, while a third step 506 can involve placing a receiver, e.g., an electro-optical receiver or laser energy detector, at a second end of the rain and fog machine 100. In a fourth step 508, a user may select a series of user inputs for a test using a control system attached to the exemplary system that may include a graphical user interface or other input/output means. The exemplary user inputs of the fourth step 508 could include a type of rain or fog event desired and a length and frequency of the device under test transmit and receive events as well as various aspects of operation of electro-optic or laser systems or other devices under test which interact with or within the rain or fog machine. Outputs of a control or testing system can include measurements of testing results to include behavior of device under test systems or outputs of all or part of device under test systems interacting within the rain or fog machine generated environment. After a user has input desired test parameters, the control module 120 could initiate a test sequence in a fifth step 510. In a sixth step 512, the control module 120 may first engage the valves and pumps of the rain and fog testing machine 100 to create the rain or fog event desired by the user. For example, the controller 120 could engage the second pump 116 and the corresponding valves to ensure that the rain and fog machine 100 is floating on the surface. The controller could then be operated to engage the first pump 104 to distribute liquid through the dispersion heads 108.

After an exemplary rain and/or fog machine 100 has been engaged to create a user desired rain or fog event, the controller 120 may be instructed to engage a device under test in a seventh step 514. The device under test could be any transmitter or receiver that may have to operate during various rain or fog events. Such devices could include electro-optical infrared transmitters/receivers, laser transmitters/receivers, and the like. The device under test may be oriented to transmit a signal from the first end of the rain and fog machine 100, through the rain or fog event created by the rain and fog machine 100, to a receiver on the second end of the rain or fog machine 100. The controller 120 can then record the transmitted and received signals to be analyzed by the user during the eighth step 516. Finally, in the ninth step 518, the controller 120 may disengage the rain or fog event by shutting off the first pump 104. Further, depending on the user inputs determined in the fourth step 508, the controller 120 may allow the buoyancy devices 202 to be submerged after the test concludes.

In addition to laser and electro-optics, devices and systems tested in a rain-fog environment created using an embodiment of the invention can also include systems which operate using other segments of the electromagnetic spectrum which can be affected by rain or fog such as radio frequency systems.

Figure 6:
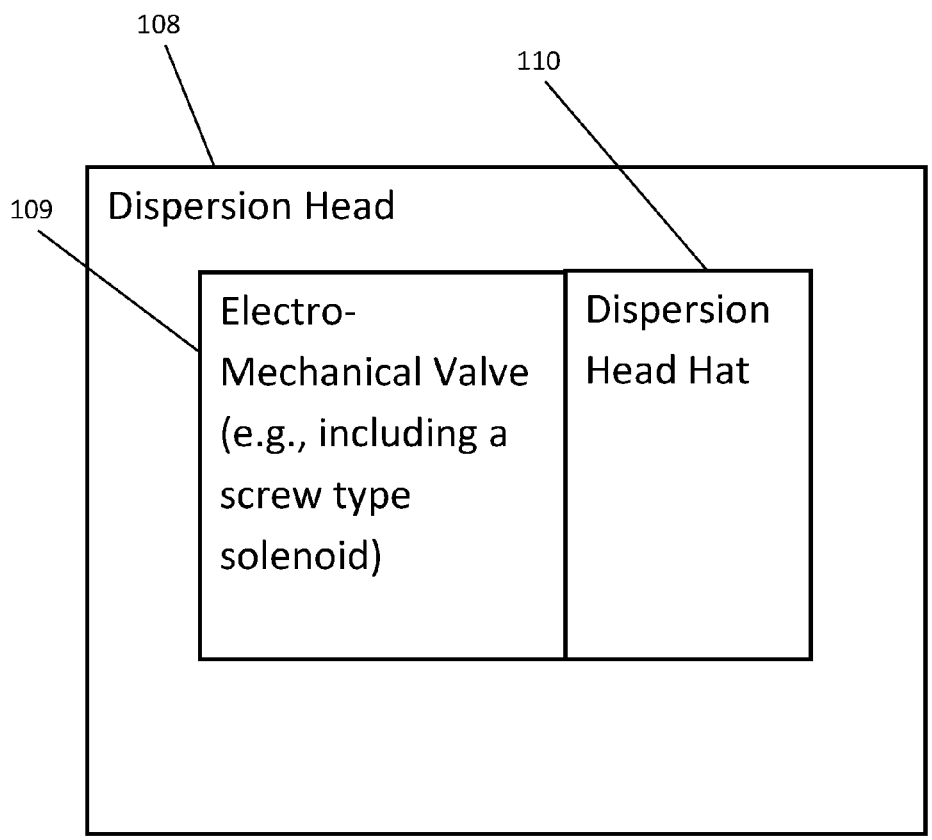
FIG. 6 shows a more detailed view of an exemplary dispersion head or nozzle described in relation to FIG. 1 and the summary section above.

Referring to FIG. 6, an exemplary dispersion head 108 (also referred to as a nozzle as discussed in the summary section above) is shown. As discussed above in the summary and paragraphs discussing dispersion heads above, the exemplary dispersion head 108 can include an individually controlled electro-mechanical screw type solenoid and a valve structure (or flow control structure) which is operated or adjusted (e.g., selectively opened or closed) by the solenoid. The control module 120 (shown in FIG. 1) can control each electro-mechanical screw type solenoid to control the valve or flow control structure within each dispersion head 108 so that the exemplary dispersion head 108 can be individually turned on or off. The dispersion heads 108 can include a dispersion head (or nozzle) hat 110 (referred to as a nozzle hat in the above summary) that may create a spray pattern that is controlled via the solenoid per commands from the control module 120 (shown in FIG. 1). An exemplary combination, such as using the dispersion head including the dispersion or nozzle head hat/solenoid combination, may allow a spray pattern to be adjusted from primarily a vertical to one that sprays primarily in a horizontal orientation.

Although the invention has been described in detail with reference to certain preferred embodiments, variations and modifications exist within the spirit and scope of the invention as described and defined in the following claims.

The invention claimed is:
1. A rain and fog testing apparatus, comprising:
a first and second fluid shutoff coupler;
a plurality of dispersion heads, wherein each of said plurality of dispersion heads comprise a valve configured to control output of the valve's respective dispersion head;
a fluid channel coupled with and disposed between said first fluid shutoff coupler and said second fluid shutoff coupler, said fluid channel is fluidly coupled with said plurality of dispersion heads, wherein said plurality of dispersion heads are configured to selectively produce a spray pattern in a pattern such that said spray pattern does not result in a gap in the spray pattern over a predetermined volume of area comprising a test area, wherein said plurality of dispersion heads are further configured to generate overlapping spray pattern portions in the spray pattern over the test area;
a liquid pump fluidly coupled to the fluid channel through one of said first or second fluid shutoff couplers;
a liquid heater configured to selectively heat liquid supplied to said plurality of dispersion heads; and
a controller that provides electrical control of the first fluid shutoff coupler, the second fluid shutoff coupler, the plurality of dispersion heads, the liquid pump, and the heater;
wherein the second fluid shutoff coupler is configured to fluidly couple said fluid channel to a plurality of additional fluid channels;
wherein the controller adjusts orientation of output from the dispersion heads by adjusting each said valve as well as operating the first fluid shutoff coupler, the second fluid shutoff coupler, the plurality of dispersion heads, the liquid pump, and the liquid heater to create a rain or fog output approximating a spray pattern simulation of one of a plurality of rain or fog events over said test area.

2. The rain and fog apparatus of claim 1, further comprising:
a first buoyancy device coupled to the fluid channel;
a first air shutoff coupler located at a first end of the first buoyancy device and fluidly coupled to an air pump; and
a second air shutoff coupler located at a second end of the first buoyancy device;
wherein the first air shutoff coupler, the second air shutoff coupler, and the air pump are controlled by the controller to open both the first air shutoff coupler and the second air shutoff coupler and engage the air pump at a user's command to fill the first buoyancy device with air;
wherein the controller opens the first air shutoff coupler and the second air shutoff coupler to allow the first buoyancy device to substantially fill with a surrounding liquid and allow the buoyancy device to become submerged within the surrounding liquid.

3. A method of controlling a rain or fog testing apparatus and corresponding device under test, comprising:
placing a rain or fog testing apparatus on a body of liquid, wherein said rain or fog testing apparatus comprises:
a first and second fluid shutoff coupler;

a plurality of dispersion heads, wherein each said plurality of dispersion heads comprise a valve configured to control output of the valve's respective said dispersion head;

a fluid channel coupled with and disposed between said first fluid shutoff coupler and said second fluid shutoff coupler, said fluid channel is fluidly coupled with said plurality of dispersion heads, wherein each of said dispersion heads are configured to selectively produce a spray pattern from the liquid in a pattern such that said spray pattern does not result in a gap in the spray pattern over a predetermined volume of area comprising a test area, said plurality of dispersion heads are further configured to generate overlapping spray pattern portions in the spray pattern over the test area;

a liquid pump fluidly coupled to the fluid channel through one of said first or second fluid shutoff couplers configured to pump said liquid into said fluid channel;

a liquid heater configured to selectively heat said liquid supplied to said dispersion heads; and a controller that provides electrical control of the first fluid shutoff coupler, the second fluid shutoff coupler, the plurality of dispersion heads, the liquid pump, and the liquid heater;

wherein the second fluid shutoff coupler is configured to fluidly couple said fluid channel to a plurality of additional fluid channels;

wherein the controller adjusts orientation of output from the dispersion heads by adjusting each said valve as well as operating the first fluid shutoff coupler, the second fluid shutoff coupler, the plurality of dispersion heads, the liquid pump, and the liquid heater to create a rain or fog output approximating a spray pattern simulation of one of a plurality of rain or fog events over said test area;

placing a transmitter at one end of the rain or fog testing apparatus, the transmitter configured and oriented to transmit a signal through a rain or fog event generated by the rain or fog testing apparatus;

placing a receiver at a second end of the rain or fog testing apparatus, the receiver configured and oriented to receive the signal transmitted through the rain or fog event;

receiving user inputs into the controller, where the user inputs determine a type of said rain or fog event and when to transmit and receive the signal;

implementing the rain or fog event determined by the user inputs by operating said rain or fog testing apparatus to create a corresponding said rain or fog event;

initiating the transmitter to send the signal through the rain or fog event and receiving the signal with the receiver; and recording the signal sent by the transmitter and received by the receiver during the rain or fog event.

4. A method as in claim 3, wherein said transmitter comprises an optical signal transmitter.

5. A method as in claim 4, further comprising:

providing and coupling a buoyancy system with said fluid channel, said buoyancy system comprising an air pump;

a first and second buoyancy device coupled to the fluid channel;

a first air shutoff coupler located at a first end of the first buoyancy device and fluidly coupled to the air pump; and a second air shutoff coupler located at a second end of the first buoyancy device;

wherein the first air shutoff coupler, the second air shutoff coupler, and the air pump are controlled by the controller to open both the first air shutoff coupler and the second air shutoff coupler and engage the air pump based on a user's control input or command to fill the first buoyancy device with air and selectively displace said liquid in said first buoyancy device so as to pump less or more air into said first buoyancy device than is within said second buoyancy device;

wherein the controller opens the first air shutoff coupler and the second air shutoff coupler to allow the first buoyancy device to substantially fill with a surrounding liquid and allow a portion or all of the first or the second buoyancy devices to become submerged within the surrounding liquid and thereby partially or completely submerge portions or all of said rain or fog testing apparatus underneath said body of liquid.

6. A rain and/or fog condition generating system, comprising:

a first and second fluid shutoff coupler;

a plurality of dispersion heads, wherein each said dispersion head comprises a valve configured to control output of the valve's respective said dispersion head;

a fluid channel coupled with and disposed between said first fluid shutoff coupler and said second fluid shutoff coupler, said fluid channel is fluidly coupled with said plurality of dispersion heads, wherein each of said dispersion heads are configured to selectively produce a spray pattern in a pattern such that said spray pattern does not result in a gap in the spray pattern over a predetermined volume of area comprising a test area, said plurality of dispersion heads are further configured to generate overlapping spray pattern portions in the spray pattern over the test area;

a liquid pump fluidly coupled to the fluid channel through one of said first or second fluid shutoff couplers;

a liquid heater configured to selectively heat liquid supplied to said dispersion heads;

a buoyancy system coupled with said fluid channel, said buoyancy system comprising a plurality of selective buoyancy structures configured to support said fluid channel above a body of fluid, an air pump, an orientation sensor configured to output an orientation data indicating orientation of the buoyancy system with respect to a body of liquid that said rain and/or fog condition generating system is placed on or within, a plurality of air shutoff couplers each comprising an air valve wherein each of said air shutoff couplers are coupled to said selective buoyancy structures configured to communicate air from the air pump into at least one of the plurality of air shutoff couplers, said buoyancy system is configured to selectively fill or release the air from within the selective buoyancy structures so that said liquid selectively enters or is selectively expelled from the selective buoyancy structures; and a controller that provides electrical control of the first fluid shutoff coupler, the second fluid shutoff coupler, the plurality of dispersion heads, the liquid pump, and the heater, wherein the controller adjusts orientation of output from the dispersion heads by adjusting each said valve or adjusting said liquid or said air in said selective buoyancy structures to alter the orientation of the buoyancy system with respect to said body of liquid, said controller further configured for operating the first fluid shutoff coupler, the second fluid shutoff coupler, the plurality of dispersion heads, the liquid pump, and the liquid heater to create a rain or fog output approximating a spray pattern simulation of one of a plurality of rain or fog events over said test area;

wherein the second fluid shutoff coupler is configured to fluidly couple said fluid channel to a plurality of additional fluid channels.

7. The apparatus as in claim 6, wherein said plurality of selective buoyancy structures comprise a first and second buoyancy tank that is coupled to said fluid channel.

* * * * *